United States Patent [19]

Auth

[11] 4,445,509

[45] May 1, 1984

[54] METHOD AND APPARATUS FOR REMOVAL OF ENCLOSED ABNORMAL DEPOSITS

[76] Inventor: David C. Auth, 4739 Somerset Ave. Southeast, Bellevue, Wash. 98006

[21] Appl. No.: 345,656

[22] Filed: Feb. 4, 1982

[51] Int. Cl.³ .............................................. A61B 17/32
[52] U.S. Cl. .................................. 128/305; 128/752; 604/266
[58] Field of Search ........................... 128/304–305, 128/749, 751–754, 757–758, 303 R; 604/22, 35, 93, 118, 164, 266

[56] References Cited

U.S. PATENT DOCUMENTS

| | | | |
|---|---|---|---|
| 2,555,493 | 6/1961 | Kirschbaum | 128/20 |
| 2,905,178 | 9/1959 | Hilzinger | 128/303 R |
| 2,955,592 | 10/1960 | MacLean . | |
| 3,074,396 | 1/1963 | MacLean . | |
| 3,525,339 | 8/1970 | Halligan | 128/303 R |
| 3,565,062 | 2/1971 | Kuris | 128/305 X |
| 3,613,664 | 10/1971 | Willson et al. | 128/303 R X |
| 3,730,185 | 5/1973 | Cook et al. | 128/303 R |
| 3,732,858 | 5/1973 | Banko | 128/305 X |
| 3,749,085 | 7/1973 | Willson et al. | 128/305 X |
| 3,811,446 | 5/1974 | Lerwick et al. | 128/303 R |
| 3,945,375 | 3/1976 | Banko | 128/305 X |
| 3,995,619 | 12/1976 | Glatzer | 128/305 X |
| 4,020,847 | 5/1977 | Clark | 128/305 |
| 4,030,503 | 6/1977 | Clark | 128/304 |
| 4,167,943 | 9/1979 | Banko | 128/305 |
| 4,167,944 | 9/1979 | Banko | 128/305 |
| 4,168,698 | 9/1979 | Ostergard | 128/305 X |
| 4,203,444 | 5/1980 | Bonnell et al. | 128/305 X |
| 4,207,874 | 6/1980 | Choy | 128/6 |
| 4,249,541 | 2/1981 | Pratt | 128/753 |
| 4,266,555 | 5/1981 | Jamshidi | 128/753 |
| 4,273,128 | 6/1981 | Lary | 128/305 |

Primary Examiner—Lee S. Cohen
Assistant Examiner—Angela D. Sykes
Attorney, Agent, or Firm—Seed and Berry

[57] ABSTRACT

A device for safe removal of abnormal deposits, primarily in the human body, where differential cutting properties provide for fracture of hard matter while safely preserving soft tissue. The device includes a rotating cutting tool having spirally shaped cutting flutes having hardness-differential cutting properties. The tool is driven from outside the body by means of a flexible drive shaft at greater than 2000 revolutions per minute. A channel is incorporated in the drive shaft for adding or removing chemical matter from the internal body space to provide systematic removal of cutting debris from abnormal deposits. The cutting tool has fluid ports which communicate with the drive shaft channel. The fluid ports may be at the nose of the tool as well as around its cicumference. In the latter instance, the ports extend from in front of a cutting flute into a center cavity with a circumferential component so that rotation tends to force blood into these ports. External mass transfer machines aid in injecting or withdrawing material, such as cutting debris. Auxiliary instrumentation, such as fluoroscopy and pressure measuring apparatus, are helpful in the clinical procedure. Multiple operational cycles are easily implemented to gradually dissect the deposit while periodically reestablishing physiological viability, such as blood flow in vessels.

32 Claims, 7 Drawing Figures

METHOD AND APPARATUS FOR REMOVAL OF ENCLOSED ABNORMAL DEPOSITS

DESCRIPTION

1. Technical Field

This invention relates to relatively noninvasive surgery and, more particularly, to a mechanical instrument for cutting hard abnormal deposits while preserving soft normal tissue.

2. Background Art

Impairment of circulation of blood by intraarterial deposits of atherosclerotic plaque (or thrombi) is a major cause of cardiovascular disease. Obstruction of coronary arteries can lead to tissue death because of oxygen deprivation of heart muscle. Coronary infarction (heart attack) is the result. Reduced blood transport in the carotid artery because of obstructive plaque can lead to transient ischemic attack (TIA) or stroke. Plaque-induced stenosis of other major arteries can result in impairment of peripheral organ function. Surgical bypass operations wherein the obstructed arteries are subtended by patient autografted vessels have become popular in recent years. Surgically invasive endarterectomy has also been used with limited success for clearing obstructed vessels.

A need exists for catheter devices which can be passed safely into the human vascular network to remove plaque deposits. No significant damage should occur to the healthy endothelial lining of the surrounding vessel. One devide that attempts to fulfill this need is the inflatable balloon that is passed to the stenotic region of the affected artery and insufflated with fluid to pressures of approximately 5 atmospheres. Some success has been claimed for this technique. Its application is limted in that nonconcentric plaque formations are relatively immune to expansion since the compliant wall of the vessel provides volumetric relief to the expanding balloon. Because circulation is grossly impaired, balloon inflation/deflation must occur in a matter of seconds to avoid infarction. For relief of partial coronary artery obstruction, balloon angioplasty has been performed with the catheter inserted in either the brachial artery or the femoral artery (Grunzig technique). Several deficiencies are present with this method. They are:

1. Limited force is available with safe pressure levels to enable expansion of the stenosis;
2. Current catheters do not provide for capture of plaque debris that may slough during the expansion process;
3. In nonconcentric lesions, the expanding balloon stretches the compliant vessel wall, thereby reducing the force which is needed to affect the plaque.

The use of a laser to clear obstructions in vessels has been proposed in U.S. Pat. No. 4,207,874, issued to Choy. In this device, laser energy is conveyed by flexible fiberoptics through a connecting artery or vein to an obstructed zone. Various axial channels are provided with appropriate fluid management manifolds in order to inject dye, suck out debris and smoke, and inject saline for visualization. Additional coherently aligned fibers are provided to actually view the obstruction intraluminally. An actual intraluminal operation of this device in a clinically relevant circumstance remains to be demonstrated. A calculation of the amount of heat required to vaporize obstructions reveals a dangerously high expenditure of calories, which, even with surface cooling by circulating water, could easily result in transmural vessel necrosis by lateral heat conduction.

Attempts have been made to insert a cutting device into a vessel to remove stenosis. However, the cutting structures used for this purpose appear to be ineffective for rapidly cutting the stenosis without damaging the relatively soft wall of the vessel. For example, U.S. Pat. No. 4,273,128 discloses a cutting device utilizing a pair of knife blades bowed outwardly from opposite sides of a drive shaft behind a forwardly projecting tip. Th structure disclosed therein would inherently cut any vessel with which it came in contact. Further, while the tip would tend to protect the vessel by spacing the blades away from the vessel, this would also prevent the device from removing substantially all of the stenosis.

U.S. Pat. No. 4,020,847 discloses a cutting catheter in which a blunt-ended cylindrical member has formed therein an elongated cutting slot, The primary disadvantages of this structure is its apparent inaability to remove a stenosis which does not have a relatively small projection that is capable of fitting into or entering the cutting slot. Utilizing a longer cylindrical member in order to allow for a larger cutting slot degrades the ability of the device to be threaded through small, curved vessels. In actuality, the primary teaching of the patent is that a stenosis can only be cut safely if the cutting edge is within the confines of a protective structure such as the tube.

U.S. Pat. Nos. 3,730,185 and 3,811,446 disclose catheter-mounted cutting devices which are adapted to remove the inner lining of a vessel along with the attached stenosis. Thus, these devices are specifically adapted to be incapable of removing a stenosis without cutting into the vessel wall.

U.S. Pat. No. 4,030,503 discloses various catheter-mounted helical structures that are screwed into a stenosis in the same manner that a corkscrew is torqued into a cork. The catheter is then pulled out, thereby theoretically removing the stenosis in the same manner that a cork is removed from a bottle.

U.S. Pat. No. 3,565,062 discloses a structure for ultrasonically removing a stenosis from a vessel.

U.S. Pat. No. 4,203,444 discloses a knee surgery cutting tool in which a semicylindrical blade is mounted at the end of a rotating shaft. The design of the blade makes it incapable of being adapted for the removal of a stenosis without damaging the walls of a vessel. The patent also teaches a system for removing cut tissue with a vacuum.

Finally, U.S. Pat. No. 3,749,085 discloses a vascular tissue-scraping device consisting of a number of helically wound wires terminated at various points by barbs. If the spiral was rotated in a direction which would tend to unwind the spiral, the wires could easily puncture the vessel. If the spiral was rotated in the other direction, any cutting force would tend to further wind the spiral, thereby decreasing the spiral's diameter and drawing it away from the stenosis.

DISCLOSURE OF INVENTION

The primary object of this invention is to remove plaque and other obstructions from organic structures by safely passing a differential cutting tool into the organ through an accessible portion of the anatomy, which cutting tool can controllably remove abnormal deposits without damage to normal tissue structure.

It is another object of this invention to provide a rotationally driven cutting tool which will preferentially abrade hard or calcified deposits while not significantly abrading normal endothelial lining.

It is another object of this invention to provide within a guiding sheath or protective sheath or rotatable drive shaft a means for injecting radiopaque fluid or other media to delineate the obstruction.

It is another object of this invention to provide within the guiding sheath or drive shaft housing or drive shaft unit a channel which will permit evacuation of abraded plaque debris or measurement of blood pressure.

These and other objects of the invention are provided by a system for removing abnormal, relatively hard deposits from a relatively soft tissue by a cutting tool utilizing differential cutting. The cutting tool is of a generally ellipsoidal configuration and it has a plurality of cutting flutes extending along its outer surface. Each cutting flute has an elongated cutting face facing in the direction of rotation so that as the cutting tool rotates, the cutting edges formed by the cutting faces cut into the relatively hard deposits. However, the angle of the cutting face with the circumference of the tool is selected so that the tool does not cut into the relatively soft vessel. Other factors, such as the number of cutting flutes and the convexity of the cutting faces, affects the hardness-differential cutting properties of the cutting tool. The cutting tool is mounted at the end of a flexible drive shaft which is enclosed for most of its length by a guiding catheter. The guiding catheter is initially inserted into the vessel from a point outside the patient's body. The cutting tool and drive shaft are then inserted through the guiding catheter to the abnormal deposit. The cutting tool is then rotated through the drive shaft by a rotary drive device, such as an electric motor, preferably operating at at least 2000 revolutions per minute. In order to remove particles of the deposit fractured by the cutting tool, the cutting tool may contain a fluid port communicating with an external suction device through a channel formed in the drive shaft. The fluid port may be at the nose of the cutting tool in order to remove blood and debris forward of the cutting tool. However, the fluid ports may also extend from in front of respective edges of the cutting flutes into a center cavity. In order to at least partially counteract the centrifugal force of the blood in these fluid ports, the ports have a circumferential component extending from the cavity in the direction of rotation so that rotation of the cutting tool has a tendency to force blood inwardly through the ports. Management of deposit debris is further enhanced by utilizing cutting flutes which extend rearwardly as well as circumferentially in a spiral configuration so that rotation of the cutting tool forces blood rearwardly into the fluid ports. A variety of external fluid management structures may be used to remove blood and debris, visually monitor its appearance, or inject fluids (such as radiopaque dye) into the vessel via the drive shaft channel and fluid ports.

BEST MODE FOR CARRYING OUT THE INVENTION

Figure 1:
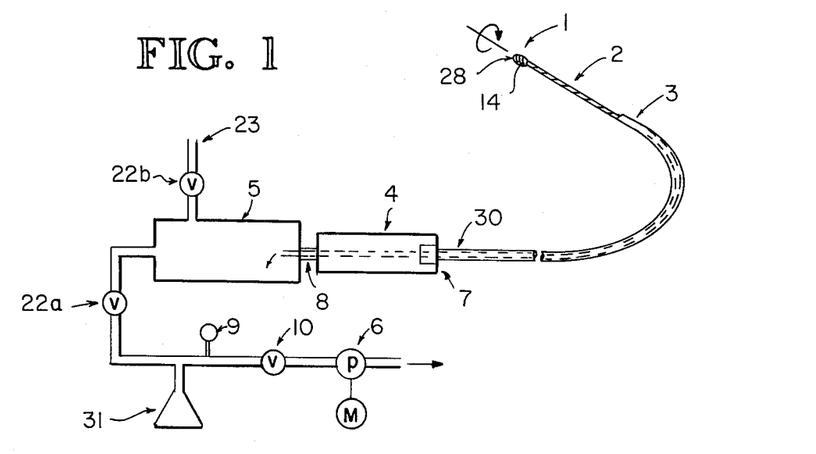
FIG. 1 is a schematic diagram illustrating a drive motor for a cutting tool which is interposed between a fluid management manifold and a flexible catheter which surrounds a drive shaft for the cutting tool.
Figure 5:
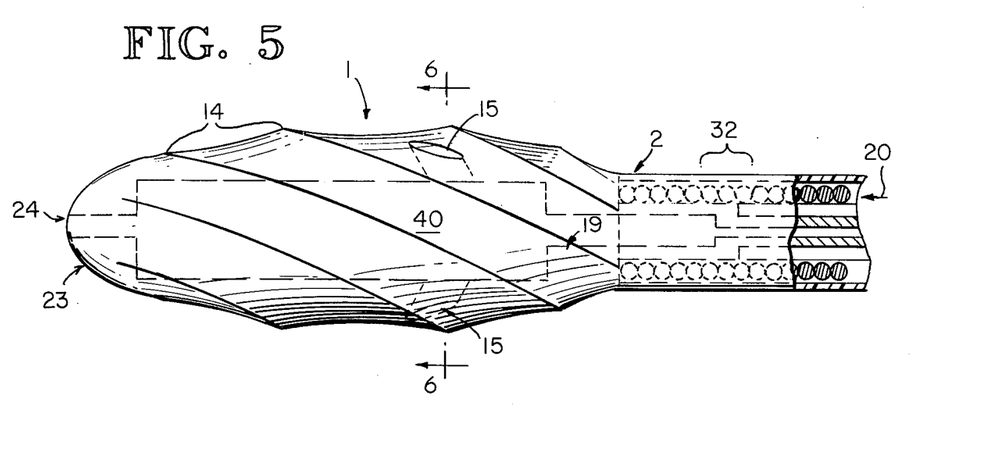
FIG. 5 schematically illustrates a rotationally driven cutting tool with fluid apertures connected to a flexible drive shaft.

One embodiment of a practical system for passing a high-rotational-speed cutting tool into a vessel to remove abnormal deposits is illustrated in FIG. 1. The cutting tool 1 is mounted at the end of a flexible drive shaft which transmits torque from a torque-generating device 4, such as an electric or pneumatic motor. The drive shaft 2 is surrounded for most of its length by a guiding catheter. In order to provide a low-friction passage of rotational motion, the outer surface of drive shaft 2 and the inner surface of guiding catheter 3 need to be of compatibly slick materials. Guiding catheters are commercially available for balloon angioplasty which have an inner lining of teflon that has been found to be excellent for this application as well. As illustrated in FIG. 5, the outer surface of the drive shaft 2 may consist of an overcoat of teflon or an actual cylindrical tube which compression-fits to an inner steel helix 20, thereby providing a fluid-tight, flexible drive shaft with good rotational strength. An inner lining of plastic tubing 21 may also be provided to improve the crush resistance of the helical steel coil. A steel helix of approximately 0.05 inch has been successful in transmitting high rotational speeds (greater than 25,000 rpm) in a controllable fashion and with mechanical security.

It is important that particles formed by the cutting tool 1 be removed from the body so that they are not carried along by the blood flowing through the vessel. As explained in greater detail hereinafter, the cutting tool 1 preferably includes fluid ports to remove particles. Thus it is important that the drive shaft be hollow so that particle-entrained blood can flow from the cutting tool 1. These fluid passages can also be used to inject fluid, such as a radiopaque media, into the vessel. Consequently, it is important to seal the hollow interior of the drive shaft until it is connected to a suction or injection device. Accordingly, the drive shaft 2 extends through the torque generator 4 and terminates in a fluid manifold 5. A seal 8 prevents fluid leakage from the manifold 5 while allowing the drive shaft 2 to rotate. The fluid manifold 5 communicates with a conventional suction device 6 when valves 22a and 10 are open. The suction may be controlled by adjusting valve 10 while monitoring a pressure gauge 9. With valve 10 closed, the pressure gauge 9 can also be used to monitor blood pressure. When the suction device 6 is being used to remove particle-entrained blood through the cutting tool 1 and drive shaft 2, the blood is drawn from the manifold 5 and collects in a fluid trap 31, which is preferably transparent so that the evacuated blood can be visually monitored. Alternatively, the valve 22a may be closed and valve 22b opened and a fluid added to the manifold 5 through injection port 23. This fluid then flows into the drive shaft 2 and out of ports in the cutting tool 1. Insofar as blood is also capable of flowing through the guiding catheter 3, the end of the guiding catheter 3 is sealed at 7 as it terminates at the torque generator 4.

Figure 2:
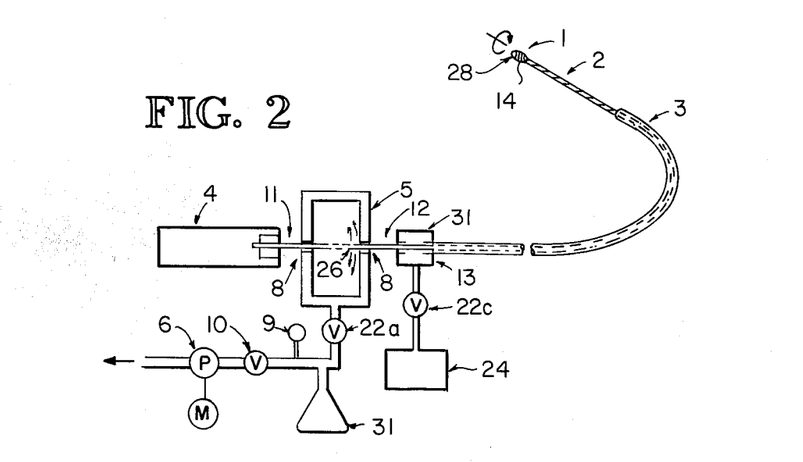
FIG. 2 is schematic diagram illustrating a plaque removal system wherein a fluid management manifold is interposed between the cutting tool drive motor and the flexible insertion catheter.

An alternative embodiment illustrated in FIG. 2 positions the fluid manifold 5 between the torque generator 4 and the cutting tool 1. In this embodiment, the guiding catheter 3 terminates in an auxiliary manifold 31 which communicates with a conventional suction device 24 when valve 22c is open. The auxiliary manifold 31 allows fluid to be removed or added through the guiding catheter 3. The end of the guiding catheter 3 passes through a seal 13, while the drive shaft 2 extends through the auxiliary manifold 31 and out through seal 12.

The drive shaft 2 then extends through seal 8 into the fluid manifold 5 through seal 8, where it is connected to the torque generator 4. The portion of the drive shaft 2 inside the manifold 5 contains a number of radial ports 26 which allow fluid communication between the hollow interior of the drive shaft 2 and the manifold 5. The shaft 2 contains a blockage downstream from the ports 26 so that fluid flowing through the drive shaft 2 flows only through the ports 26.

As with the fluid manifold 5 of FIG. 1, the fluid manifold 5 of FIG. 2 is connected to a suction device 6 through valves 22a and 10, thereby allowing fluid to collect in fluid trap 31. The fluid manifold 5 of FIG. 2 may also include the injection port 23 and valve 22b of FIG. 1. And, of course, the embodiment of FIG. 1 could utilize the auxiliary manifold 30 of FIG. 2 positioned in front of the torque generator 4.

Figure 7:
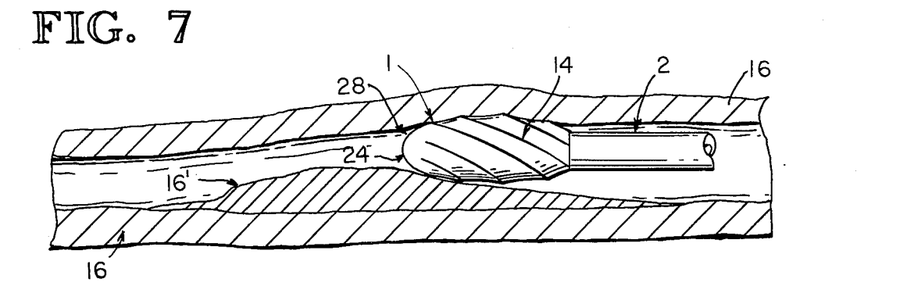
FIG. 7 illustrates the cutting tool is use during an intraluminal plaque removal operation.

As illustrated in FIG. 7, the cutting tool 1 and guiding catheter 3 are inserted into a vessel 15 containing a stenosis 16. The torque-generating unit 4 may be either electric or compressed-air powered. Studies to date have used electrically powered units. When using a steel(metal)-reinforced drive shaft 2, there can be a shock hazard to the patient would could be more easily avoided with the use of an air-powered unit 4. In order to eliminate shock hazard with the electrically powered unit 4, the catheter drive shaft 2 should be electrically isolated with respect to the electric motor and the flexible drive shaft 2. Shock hazard is especially worrisome when working in the coronary arteries since currents as small as 100 microamps can cause fibrillation when directly impressed on cardiac tissue. Other electrical safeguards should be employed to prohibit the possibility of electrical currents being conveyed via the metal reinforcing structure of the drive shaft.

It is important for controllable entry of the cutting tool 1 into an obstructive lesion that it be advanced predictably. Thus, to facilitate such cutting tool advance, the drive shaft 2 should be axially translatable with respect to the guiding catheter 3. Seals 7, 8 and 12, therefore, need to slide axially as well as circumferentially. In practice, it has been found that manual retraction of the guiding catheter 3 results in well-controlled advance of the cutting tool 1 at the distal end. The tool 1 may be gently nudged into a stenosed area during rotation and then retracted to permit evacuation of residual debris and to reestablish local circulation before making another cutting cycle on the lesion. In conjunction with fluoroscopic surveillance and injection of radiopaque dye through the cutting tool 1, controlled progress in opening of the obstruction is possible.

Cutting tool 1 has been configured in a generally elliptical shape which enables controlled insertion into a stenosed vessel 15. The nose 28 is polished to avoid unwanted snagging of the nose of the tool when negotiating anatomical curves. Various sizes have been fabricated in accordance with the vessel size and severity of the stenosis. In general, the range of useful diameters is from 1.0 to 3.5 mm. The extent of the nose polishing is determined by the particular vessel to be cleaned; for example, for a severe stenosis, a useful choice for the polished nose diameter is 0.5 mm with six cutting flutes 14 on the circumference of the cutting ellipse. The maximum outside diameter would be 1.2 mm, the cant angle could be 100 degrees, and the length could be about 2.5 mm. In a typical procedure, it may be necessary to use two or three different tip/catheter units to bring a very heavily stenosed vessel up to a 3 mm inside diameter. This is easily facilitated once the guiding catheter 3 is placed within the body. As explained above, the guiding catheter 3 contains a hollow channel 30 which provides for subsequent insertion and withdrawal of several instruments during the course of a procedure without the difficult task of rethreading the particular branch of the cardiovascular network. The guiding catheter is inserted transmurally through an accessible vessel which connects with the stenotic lesion.

It is apparent from FIG. 7 that the cutting tool 1 must have the property of cutting through the stenosis 16 without significantly cutting or abrading the internal walls of the vessel 15. This is particularly critical because the cutting flutes 14 of the cutting tool 1 contact the walls of the vessel 15 with the same force that they contact the stenosis 16. This problem is solved by the principle of hardness differential cutting by which the cutting tool 1 easily cuts relatively hard material, such as calcific plaque, but does not cut relatively soft material, such as the vessel 15.

Figure 3:
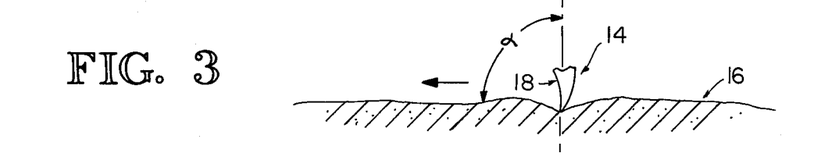
FIG. 3 is a schematic diagram illustrating the discriminatory cutting action of a properly pitched cutting tool wherein soft normal tissue is relatively undamaged.
Figure 4:
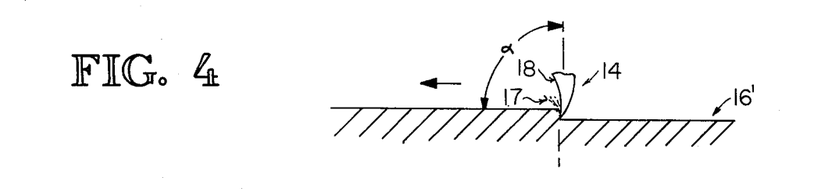
FIG. 4 is a schematic diagram illustrating the discriminatory cutting action of a properly pitched cutting tool wherein hard abnormal deposite (plaque or other hard mineral deposit) is abraded as shown.

The physics of differential cutting is explained with the aid of FIGS. 3 and 4. In FIG. 3, a cutting blade 14 having a cutting face 18 is moving from right to left over the surface of soft and preferably wet tissue 16. The cutting blade 14 is touching the soft tissue 16 and is deflecting it from its unperturbed state. Because the soft tissue 16 has a relatively low value of shear modulus of elastic stiffness, it undergoes marked deformation in the region proximate to the tip of the cutting blade as a result of the blade depression and the small amount of tangential frictional drag associated with relative motion. Because of the compliance of the soft tissue 16, large shear stresses cannot be supported within the tissue matrix. Since large stresses are avoided in this configuration of blade/soft-tissue interface, the tissue 16 will not undergo compressive fracture and thus no abrasion occurs. In contrast, FIG. 4 depicts the case of blade passage over relatively rigid material 16', such as calcific plaque. Again, the blade moves from right to left in the diagram. Because of the high value of shear modulus of elastic stiffness, the rigid material 16' is unable to comport itself to reduce the peak values of tangental pressure. Thus, instead of reshaping its local matrix and slipping underneath the cutting blade, it is trapped in front of the blade, and large compressive stresses arise. These stresses are large enough to cause compressive fracture of the rigidified matter. As a reult, tiny fragments 17 of the rigid matter are expelled at the cutting edge of the blade 14 with resultant abrasion of the rigid matter 16'. This method of differential cutting is central to this invention because it permits the cutting tool to be inserted into a vessel containing a stenosis (as shown in FIG. 7) with one side safely impacting upon the normal intimal lining of a vessel, while at the same time the other side is forced onto the surface of the plaque with resultant cutting of the plaque. Because the forces are relatively small, the amount of material removed with each passage of the blade is microscopically small. Operating at high rotational speeds (greater than 25,000 rpm), it is possible to quickly remove a millimeter of rigid matter without causing significant damage to the normal endothelium. Such a system has been tested at a rotational speed of 27,000 rpm conveyed through a commercial, teflon-lined, flexible, cardiovascular guiding catheter. The catheter was able to withstand the torque transmission without any detectable heating or other difficulty. When the bit was placed against the inner lining of the inventor's mouth, no discernible pain or damage was detected during or after the application at 27,000 rpm. The same tool bit was able to rapidly and controllably abrade stiff material, such as a fingernail or cadaver plaque.

In order to assure cutting differentiation, the necessary longitudinal and shear forces required to force the soft, compliant material to dive beneath the cutting edge (see FIG. 3) must be lower than those necessary to create mechanical fracture. Several design parameters need to be considered in assuring the proper range of shear forces for safe operation. If the circumferential flute density (i.e., the number of flutes per circumferential length) is too low in combination with a large cant angle ($\alpha$) of the cutting face 18, the blade can catch even on soft tissue and rapid abrasion is the result. If the cutting face of the blade 14 is heavily curved such that the microscopic cant angle at the tissue interface is too large, the blade can again cause soft tissue abrasion. Finally, the microscopic sharpness of the cutting edge can affect the ability of soft tissue to dive underneath the blade, as seen in FIG. 3. However, the sharpness of the blade, while affecting the hardness-differential cutting properties, is of secondary importance since the cutting properties are principally controlled by cant angle and flute density. The key, then, is to provide a blade having a flute density and cant angle selected to abrade a relatively hard stenosis without abrading the relatively soft vessel.

Figure 6:
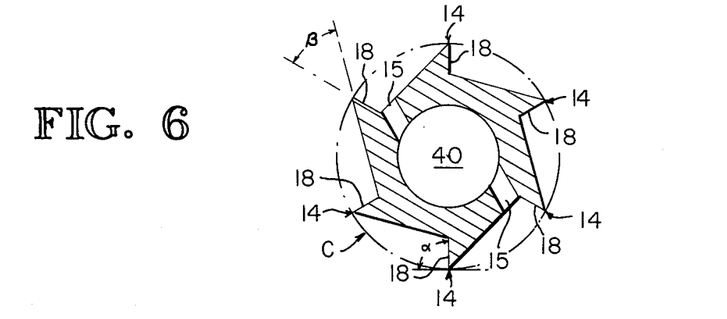
FIG. 6 is a cross-sectional view taken along the line 5—5 of FIG. 4.

The cutting tool is illustrated in some detail in FIGS. 5 and 6. The tool 1 is mounted on the drive shaft 2 through a coupling sleeve 19 which provides fluid coupling between the hollow interior 40 of the tool 1 and the hollow interior of the drive shaft 2.

Fluid passage into or out of the cutting tip may be accomplished through radial ports 15 or end port 24 (see FIG. 5). End port 24 is important for collecting cutting debris when the catheter 3 is inserted upstream from the lesion since the natural flow pattern takes the particles downstream to the port 24. Radial ports 15 are useful as additional scavengers of debris and as an aid to keeping the cutting flute 14 clean. Either set of ports 15,24 may be used for injecting dye or for sampling blood or for injecting chemicals which may be useful for dissolving emboli.

The spinning cutting tool 1 has a tendency to propel the fluid outward from ports 15 due to centrifugal force. This feature is utilized in the design of centrifugal fluid pumps but can work against the proximal transport of fluid in this invention. For a cutting tool 1 with a maximal diameter of 3 mm, the centrifugal component of fluid pressurization is equal to atmospheric pressure at approximately 50,000 rpm. Thus, in clincal use, this component of fluid pressure can be a distinct disadvantage, depending on the tool speed. However, two features are incorporated to address the centrifugal force problem and enhance the fluid flow pattern in the proximal direction. These are integrated turbine pump action and suction. There is a dual angular sweep in the fluid port 15, as indicated in FIGS. 5 and 6. Since FIG. 6 depicts the cutting tool as seen from the rear when the tool is rotated in the right-hand direction (clockwise as seen from the rear), the fluid is pushed into the center cavity 40 of the tool 1 because of the circumferential component of the fluid ports 15. At the same time, because the fluid ports 15 have a rearward or longitudinal component, the fluid is propelled rearwardly or proximal. This transfer of momentum to the fluid system during rotation assures the blood pressure and the suction in transporting blood and debris rearward and out of the body. Rearward movement of debris-entrained blood is further enhanced by the spiral configuration of the cutting flutes 14, which sweep the blood rearwardly into the extending ports 15. Observation of transparent reservoir 31 provides continuous surveillance of fluid transport features. During cutting at high speeds, the centrifugal pump action reduces the fluid pressure differential, forcing debris inward so that it can be removed by suction through the hollow interior of the drive shaft 2. In the event that the flutes 14 of the cutting tool 1 become clogged with debris, the cutting tool 1 can be spun backwards at very high speeds in order to reversethe turbine effect and propel the debris outwardly by centrifugal force. Suction would then continue to be applied so that expelled debris would be evacuated by port 24. Providing constant aspiration of debris is normally considered desirable even though the particle size of debris can be much smaller than a micron when the cutting tool is spun at greater that 25,000 rpm. Such small debris particles may not cause distal embolic complications. This is subject to further detailed biological studies.

As mentioned above, it is important to select a flute density and cant angle which will cause the blade or flute 14 of the cutting tool to abrade the relatively hard stenosis yet not abrade the relatively soft wall of the vessel. Insofar as the edges of the flutes 14 move in a circular path, the cant angle is the angle $\alpha$ of intersection of the cutting face 18 and the circumference C at the point of contact therebetween. This angle is preferably about 110 degrees, although deviations from that angle of at least 20 degrees are acceptable. Preferably, the face 18 of the flute 14 also has a slight concave curvature which affects the cant angle. The angle $\alpha$ between the leading and trailing edges of the flute 14 affects its durability. Larger angles $\alpha$ make the flute 14 more durable, but they also adversely affect the pumping action of the flutes 14. Thus, a balance must be reached between durability and pumping action.

Although the cutting tool 1 disclosed herein utilizes six flutes 14, it will be understood that the flute density or number of flutes may vary as desired. A larger number of flutes causes the cutting tool 1 to take shallower bites, thereby ensuring greater protection against cutting soft vessel tissue while also tending to produce smaller particles of debris, which have a less harmful effect if they are not removed from the vessel. On the other hand, the smaller number of flutes 14 inherently positions the flutes 14 farther apart from each other, thereby reducing the tendency of the cutting tool 1 to become clogged with debris. In practice, the number of flutes 14 may depend upon the transverse diameter of the cutting tool 1. Where the stenosis is removed with successively larger cutting tools, the number of flutes in the tools can be successively increased.

I claim:

1. A cutting tool for removing abnormal deposits, comprising a cylindrically symmetric body having a center cavity and a nose, at least one cutting flute extending along the outer surface of said body each cutting flute having a circumferentially facing cutting face formed thereon, and a radial fluid port extending from in front of a respective face of a flute into said center cavity, each port having a circumferential component extending into said cavity away from said cutting face whereby rotation of said cutting tool within a blood vessel about the major axis of said body has a tendency to force blood inwardly through said port.

2. The cutting tool of claim 1, further including a nose fluid port extending along said major axis from the nose of said body to said center cavity.

3. The cutting tool of claim 2 wherein each flute terminates before reaching said nose and said nose is polished to a smooth finish.

4. The cutting tool of claim 2 wherein each radial fluid port has a component extending along said major axis in a direction away from said nose so that fluid flows into said cavity away from said nose fluid port.

5. The cutting tool of claim 4 wherein each flute extends rearwardly and circumferentially away from said nose in a spiral configuration so that rotation of said cutting tool within a blood vessel has a tendency to force debris-entrained blood away from said nose and into said radial fluid port.

6. The cutting tool of claim 1 wherein the angle between the cutting face of each flute and the circumference around said body is between 90 and 130 degrees in order to maximize the ability of said cutting tool to remove relatively hard substances without cutting relatively soft material.

7. The cutting tool of claim 1 wherein each flute extends rearwardly and circumferentially from one end of said body to the other in a spiral configuration so that rotation of said cutting tool within a blood vessel in the forward direction has a tendency to force blood along the outer surface of said body.

8. A system for removing abnormal, relatively hard deposits from a relatively soft vessel, comprising:
a generally cylindrically symmetric cutting tool having a diameter that is smaller than the lumen of said vessel, said cutting tool having a nose and at least one cutting blade extending along an outer surface thereof, said at least one cutting blade being substantially exposed, each cutting blade having a cutting face intersecting the other surface of said tool at an angle causing fracture of said relatively hard deposits without cutting said relatively soft vessel;
a flexible drive shaft having one end connected to said cutting tool, said shaft having a length that is sufficient to reach from a point outside of a patient's body through said vessel to said abnormal deposit;
a flexible guiding catheter surrounding said drive shaft over most of its length; and
rotary drive means connected to said drive shaft to rotate said cutting tool in the direction that said cutting face if facing.

9. The system of claim 8 wherein said drive shaft contains a hollow channel and said cutting tool includes at least one fluid port communicating with said channel, said system further including a suction device communicating with said channel to draw blood and deposit debris, forming debris entrained blood, into said fluid port and through said channel.

10. The system of claim 9 wherein said drive shaft extends through said rotary drive means and terminates in a fluid manifold that communicates with said suction device.

11. The system of claim 10, further including a fluid trap communicating with said manifold for collecting said debris-entrained blood.

12. The system of claim 10, further including means for selectively preventing said suction device from applying a vacuum to said fluid manifold and wherein said manifold further includes an injection port for inserting fluid into said vessel through said manifold, drive shaft channel, and cutting tool fluid port.

13. The system of claim 9 wherein said drive shaft extends through a fluid manifold into said rotary drive means and a portion of said drive shaft within said fluid manifold includes a fluid port allowing fluid communication between said manifold and said hollow channel.

14. The system of claim 13, further including a fluid trap communicating with said manifold for collecting said debris-entrained blood.

15. The system of claim 9, further including an auxiliary fluid manifold through which said drive shaft passes, said auxiliary fluid manifold communicating with the interior of said catheter.

16. The system of claim 15, further including a second suction device communicating with said auxiliary fluid manifold to remove blood from said catheter.

17. The system of claim 9 wherein said cutting tool has a central cavity and said fluid port extends from in front of a respective edge of a cutting blade into said center cavity, said port having a circumferential component extending into said cavity in the direction opposite the direction of rotation whereby rotation of said cutting tool within a blood vessel about the major axis of said cutting tool has a tendency to force blood inwardly through said port.

18. The system of claim 17, further including a nose fluid port extending along said major axis from the nose of said tool to said center cavity.

19. The system of claim 18 wherein each blade terminates before reaching said nose and said nose is polished to a smooth finish.

20. The system of claim 18 wherein each fluid port has a component extending along said major axis in a direction away from said nose so that fluid flows into said cavity away from said nose fluid port.

21. The system of claim 20 wherein each blade extends rearwardly and circumferentially away from said nose in a spiral configuration so that rotation of said cutting tool within a blood vessel has a tendency to force blood away from said nose and into said fluid port.

22. The system of claim 9 wherein said cutting tool has a central cavity and said fluid port extends from the nose of said cutting tool into said cavity along the major axis of said cutting tool.

23. The system of claim 8 wherein the angle between the cutting face of each flute and the circumference of said cutting tool is between 90 and 130 degrees in order to maximize the ability of said cutting tool to remove said relatively hard deposits without cutting said relatively soft vessel.

24. The system of claim 8 wherein each blade extends rearwardly and circumferentially from one end of said cutting tool toward the other in a spiral configuration so that rotation of said cutting tool within said blood vessel has a tendency to force blood along the outer surface of said cutting tool toward said drive shaft.

25. The system of claim 8 wherein said rotary drive means rotates said cutting tool at at least 2000 rpm.

26. A method of removing relatively hard, abnormal deposits from a relatively soft vessel, comprising:
inserting a guiding catheter into said vessel from a point outside the body of a patient;
inserting a cutting tool mounted on a flexible drive shaft into said guiding catheter and positioning said cutting tool adjacent said deposit, said cutting tool having at least one cutting blade extending along an outer surface thereof, each blade having a cutting face intersecting an outer surface of said tool at an angle causing said cutting face to abrade said abnormal deposits without cutting said relatively soft vessel; and
rotating said drive shaft.

27. The method of claim 26 wherein said drive shaft is rotated at a speed greater than 2000 rpm.

28. The method of claim 26, further including the steps of successively withdrawing said drive shaft and cutting tool and reinserting a drive shaft having a cutting tool of a successively larger diameter until a sufficient amount of said deposit has been removed.

29. The method of claim 26 wherein said cutting tool has a least one fluid port and said drive shaft has a hollow channel communicating with said fluid port, said method further including the step of withdrawing blood and deposit debris through said fluid port and hollow channel.

30. A cutting tool for removing relatively hard abnormal deposits positioned adjacent to relatively soft body tissues, comprising;
a generally cylindrical symmetric body having at least one cutting blade projecting therefrom, said cutting blade being substantially exposed, and attaching means at one end thereof for securing said cutting tool to a rotating drive shaft, said cutting blade having a cutting face intersecting an outer surface of said body at an angle causing fracture of said abnormal deposits without cutting said body tissues at the frequency that said tool is adapted to rotate.

31. The cutting tool of claim 30 wherein each cutting blade comprises a cutting blade extending circumferentially in a spiral configuration so that rotation of said cutting tool within a blood vessel has a tendency to force blood axially along said tool.

32. The cutting tool of claim 30 wherein the angle between the cutting face of each blade and the circumference around said body is between 90 and 130 degrees in order to maximize the ability of said cutting tool to remove said abnormal deposits without cutting said body tissues.

* * * * *

UNITED STATES PATENT AND TRADEMARK OFFICE
CERTIFICATE OF CORRECTION

PATENT NO. : 4,445,509

DATED : May 1, 1984

INVENTOR(S) : David C. Auth

It is certified that error appears in the above-identified patent and that said Letters Patent is hereby corrected as shown below:

Title page, item [57]:
ABSTRACT, line 15, "cicumference" should read -- circumference --.

Column 1, line 31, "devide" should read -- device --.

Column 1, line 36, "limted" should read -- limited --.

Column 2, line 10, "Th" should read -- The --.

Column 2, line 18, "slot," should read -- slot. --.

Column 4, line 12, "5-5" should read -- 6-6 --, and

"4" should read -- 5 --.

Column 4, line 13, "is" should read -- in --.

Column 4, line 30, "teflon" should read -- TEFLON® --.

Column 4, line 33, "teflon" should read -- TEFLON --.

Column 5, line 34, "manifold 30" should read -- manifold 31 --.

Column 5, line 37, "vessel 15" should read -- vessel 16 --.

Column 5, line 38, "stenosis 16" should read -- stenosis 16' --.

Column 6, line 5, "vessel 15" should read -- vessel 16 --.

Column 6, lines 30 and 35, "stenosis 16" should read

-- stenosis 16' --.

UNITED STATES PATENT AND TRADEMARK OFFICE
CERTIFICATE OF CORRECTION

PATENT NO. : 4,445,509

DATED : May 1, 1984

INVENTOR(S) : David C. Auth

It is certified that error appears in the above-identified patent and that said Letters Patent is hereby corrected as shown below:

Column 6, lines 32, 34, and 39, "vessel 15" should read
-- vessel 16 --.

Column 6, line 66, "reult" should read -- result --.

Column 7, line 15, "teflon-lined" should read -- TEFLON-lined --.

Column 8, lines 54 and 56, "$\alpha$" should read -- $\beta$ --.

Claim 1, line 4, "body" should read -- body, --.

Claim 8, line 9, "other" should read -- outer --.

Claim 8, line 10, "causing" should read -- for causing --.

Claim 8, line 22, "if" should read -- is --.

Claim 9, line 3, "one" should read -- one radial --.

Claim 15, line 1, "9" should read -- 10 --.

Claim 17, line 4, "center" should read -- central --.

Claim 18, line 3, "center" should read -- central --.

UNITED STATES PATENT AND TRADEMARK OFFICE
CERTIFICATE OF CORRECTION

PATENT NO. : 4,445,509

DATED : May 1, 1984

INVENTOR(S) : David C. Auth

It is certified that error appears in the above-identified patent and that said Letters Patent is hereby corrected as shown below:

Claim 23, line 2, "flute" should read -- blade --.

Claim 24, line 4, "said" should read -- a --.

Claim 26, line 11, "causing" should read -- for causing --.

Claim 30, line 10, "causing" should bead -- for causing --.

Signed and Sealed this

Thirtieth Day of November, 1993

Attest:

BRUCE LEHMAN

*Attesting Officer*  *Commissioner of Patents and Trademarks*